United States Patent [19]
Berger et al.

[11] Patent Number: 5,238,928
[45] Date of Patent: Aug. 24, 1993

[54] METHODS AND MATERIALS FOR OBTAINING PHENOTYPIC FEMALES DESPITE ANDROGEN ADMINISTRATION

[75] Inventors: Larry L. Berger; Darrel Kesler, both of Champaign, Ill.

[73] Assignee: Board of Trustees of the University of Illinois, Urbana, Ill.

[21] Appl. No.: 774,584

[22] Filed: Oct. 10, 1991

Related U.S. Application Data

[63] Continuation-in-part of Ser. No. 499,565, Mar. 26, 1990, abandoned, which is a continuation of Ser. No. 312,509, Feb. 17, 1989, abandoned, which is a continuation of Ser. No. 891,158, Jul. 28, 1986, abandoned.

[51] Int. Cl.⁵ .............................................. A61K 31/56
[52] U.S. Cl. .................................... 514/179; 514/177
[58] Field of Search ........................ 514/177, 178, 179

[56] References Cited

PUBLICATIONS

Clarke et al., "Effects of testosterone implants in pregnant ewes on their female offspring"*J. Embryol Exp Morph* 36(1):87–99 (1976).
Chem Abst. 85:172096 (1976).
DeHaan et al. Abst. J. Animal Sci 63(sup 1):213 Jul. 28, 1986.

Primary Examiner—Frederick E. Waddell
Assistant Examiner—Gregory Hook
Attorney, Agent, or Firm—Delphine M. Kranz

[57] ABSTRACT

Methods for producing phenotypic female mammals intended for human or animal consumption despite androgen administration to obtain the benefits thereof, which methods include prenatally exposing said female mammals to androgen by administering to the mother an effectively constant amount of androgen sufficient to achieve and maintain a level of circulating androgen in the mother's bloodstream approximately equivalent to that of a normal adult male of the same species.

8 Claims, 1 Drawing Sheet

METHODS AND MATERIALS FOR OBTAINING PHENOTYPIC FEMALES DESPITE ANDROGEN ADMINISTRATION

This application is a continuation-in-part of U.S. Ser. No. 07/499,565, filed Mar. 26, 1990, now abandoned, which in turn is a file wrapper continuation of U.S. Ser. No. 07/312,509, filed Feb. 17, 1989, now abandoned, which in turn is a continuation of U.S. Ser. No. 06/891,158, filed Jul. 28, 1986, now abandoned.

This invention pertains in general to methods of producing female mammals of the type normally slaughtered at adulthood to obtain meat suitable for human or animal consumption, and in particular to methods which obtain phenotypic female offspring by administering to the mother of the offspring during the prenatal period an effectively constant amount of androgen sufficient to achieve and maintain but not exceed a level of circulating androgen in the mother's bloodstream approximately equivalent to that of a normal adult male of the same species.

The key to improving the economic competitiveness of mammals as sources of proteins in the human and/or animal diet lies in improving the carcass merit (relative ratio of lean meat to fat), growth rate, and feed efficiency (i.e., decreasing the amount of feed required per unit of weight gain). Heifers grow approximately 12 to 15% slower and are 10 to 12% less efficient in converting feed to weight gain than intact male herd-mates. Similarly, ewe lambs grow approximately 6 to 8% slower and require 4 to 6% more feed per unit of gain than intact ram lambs. Heifers routinely produce carcasses which are worth two to three dollars less per hundred pounds, compared to steer carcasses. This is due to the higher fat content, lower lean yield and lighter weight of heifer carcasses compared to steer carcasses of similar quality grade. The cause for these differences between the sexes in growth rate, feed efficiency, carcass merit, and meat quality is not clearly understood.

SUMMARY OF THE INVENTION

According to the present invention, a method for obtaining phenotypically female offspring despite androgen exposure during gestation includes administering to a pregnant female by about mid gestation an amount of androgen effective for obtaining an effectively constant amount of androgen approximately equivalent to that of a normal adult male wherein the male and female are from the same species selected from the group consisting of bovine, ovine, and porcine mammals, whereby a birth weight less than an average birth weight of untreated females is obtained. When the administration includes exposing the pregnant female to the androgen by about the initiation of sexual development, increases in carcass merit, feed efficiency and growth rate, and fertility control may be achieved. The present invention provides a method for producing females despite androgen administration whereby all females produced are phenotypically female.

When the administration includes maintaining the circulating level of androgen in the upper half of a range of androgen levels of the normal adult male, and preferably includes controlling the circulating level of androgen to be in the uppermost quarter of the range, sterile offspring may be obtained.

Alternatively, when the administration includes maintaining the circulating level of androgen in the lower half of a range of androgen level of the normal adult male, and preferably includes controlling the circulating level of androgen to be in the lowermost quarter of the range, fertile female offspring may be obtained.

When the female mammal is a bovine female, the amount of androgen administered is preferably calculated to maintain the circulating blood levels of androgen at approximately the level of a normal adult bull of about 0.5 to about 15 ng/ml, and more preferably about 2 to about 10 ng/ml.

When the female mammal is an ovine female, the dosage of androgen is calculated to maintain the circulating blood level of androgen at approximately the level of a normal adult ram of about 0.5 to about 15 ng/ml, and, more preferably, preferably, about 2 to about 7 ng/ml.

When the female mammal is a porcine female, the dosage of androgen is calculated to maintain the circulating blood levels of androgen at approximately the level of a normal adult boar of about 1 to about 20 ng/ml, and, more preferably, about 2 to about 8 ng/ml.

Preferably, administration of androgen may be begun prior to the time of initiation of sexual development. Administration may also be begun by about mid gestation.

Administration of androgen may be maintained through the end of gestation, through the second third of gestation, or through mid gestation, but it is more preferably maintained through about one week before parturition and most preferably the administration of androgen is maintained for 14–30 days.

The term "a level of circulating androgen approximately equivalent to that of a normal adult male" as used herein means the daily average level of androgen in the bloodstream of a fertile male as measured by immunoassay (preferably radioimmunoassay or enzyme immunoassay). Included within the meaning of this term is the understanding that such immunoassays commonly exhibit a variability of 1–2 ng.

The term "phenotypically female" as used herein means that, upon gross anatomical observation, the genitalia exhibit female but not male characteristics.

BRIEF DESCRIPTION OF THE DRAWINGS

The Figure is a graph of circulating testosterone concentration (in ng/ml of blood) versus time after administration in hours and days for a comparison of testosterone-containing pellets with silicone implants containing testosterone.

DETAILED DESCRIPTION

Figure 1:
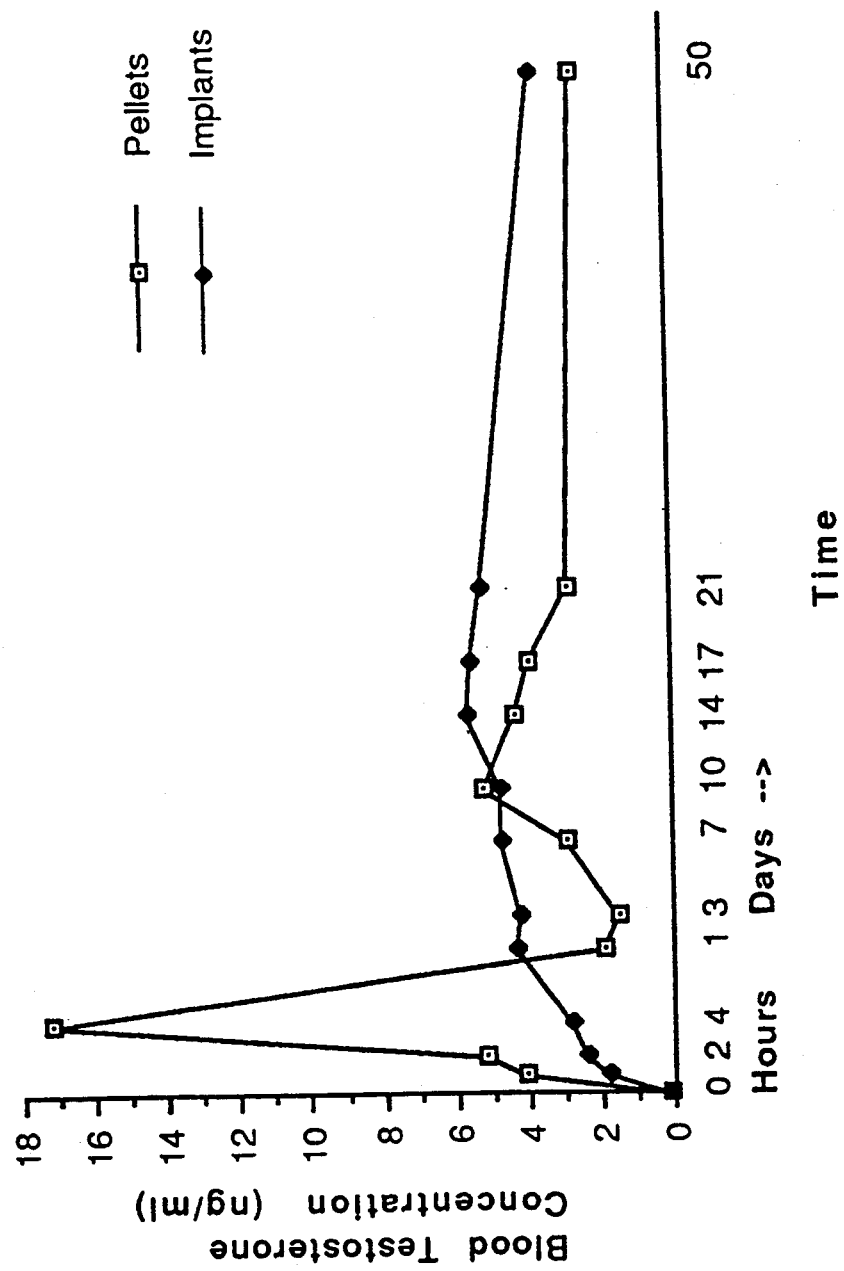

According to the present invention, the carcass merit of female mammals may be improved by exposing a female mammal solely during its prenatal period to androgens. This is conveniently done by administering to the mother of the female mammal during pregnancy and by about the time of initiation of sexual differentiation of the offspring an effectively constant amount of androgen sufficient to achieve and maintain but not exceed a level of circulating androgen in the mother's bloodstream approximately equivalent to that of a normal adult male of the same species. According to the methods of the present invention the levels of sex hormones in the female offspring may be normal after birth, thus also avoiding having unnatural elevated levels of sex hormones present in the animal to be slaughtered and consumed.

According to the present invention, the feed efficiency of female mammals is improved by exposing the female mammal solely during its prenatal period to androgens by administering to the mother during gestation and by about the time of initiation of sexual differentiation of the offspring an effectively constant amount of androgen sufficient to achieve and maintain but not exceed a level of circulating androgen in the mother's bloodstream approximately equivalent to that of a normal adult male of the same species. With this approach the animal to be consumed is itself need not be implanted; exposure during gestation via the mother is effective for the offspring's entire life.

The advantages of the present invention are obtained without the undesirable side effects associated complete masculinization of the external genitalia, i.e., the androgenized offspring are phenotypically female. According to the present invention, the growth rate in female mammals is enhanced by exposing the female mammal solely during its gestation to androgens by administering to the mother during gestation and by about the time of initiation of sexual differentiation of the offspring an effectively constant amount of androgen sufficient to achieve and maintain but not exceed a level of circulating androgen in the mother's bloodstream approximately equivalent to that of a normal adult male of the same species.

According to the present invention, the birth weight of female mammals can be reduced to a level below the average birth weight for untreated mammals of the same species by exposing the female mammal solely during its gestation to androgens by administering to the mother during pregnancy by about mid gestation an effectively constant amount of androgen sufficient to achieve and maintain but not exceed a level of circulating androgen in the mother's bloodstream approximately equivalent to that of a normal adult male of the same species. Lowered birth weight reduces dystocia, improves the efficiency of production by increasing the number of offspring weaned per mother and shortens the interval from delivery to first estrus in the mother.

According to the present invention, the problems associated with fertility can be controlled by partial masculinization of the female mammal, produced by exposing said female mammal solely during its gestation to androgens by administering to the mother during pregnancy an effectively constant amount of androgen sufficient to achieve and maintain a level of circulating androgen in the mother's bloodstream approximately equivalent to that of a normal adult male of the same species. By administering androgens by about the initiation of sexual differentiation, an increased proportion of sterile female mammal offspring may be achieved by administering androgen to the mother to obtain a circulating level within the upper half, and preferably within the uppermost quarter, of the range of normal male androgen levels. Alternatively, fertile female mammal offspring may be obtained by administering to the mother to obtain a circulating level within the lower half, and preferably within the lowest quarter, of the range of normal male androgen levels.

The method of the present invention is suitable for use with any female mammal intended for human or animal consumption, including but not limited to horses, bison, deer, reindeer, goats, rabbits, and so forth, but in particular as applied to cattle, sheep and pigs.

Androgens suitable for use in this invention are male steroids capable of causing the biological changes that normally occur during in-utero sexual differentiation of the developing male offspring, e.g. androstenediones, testosterone and derivatives of testosterone such as dihydrotestosterones, 19-nortestosterone, and their derivatives, especially their esters, such as testosterone propionate, testosterone cypionate, and the like. Testosterone and derivatives of testosterone, e.g. testosterone propionate, are preferred.

The compositions of the present invention are administered to the mother during pregnancy in any convenient manner, for example by implant under the skin, e.g. in the ear lobe, in skin folds, or in the neck of the animal. Instead of implants, the compositions may be injected intravenously, intramuscularly, subcutaneously, or intraperitoneally in the form of a time-release preparation. The compositions of the present invention may also be deposited intraocularly as a gel or foam or intravaginally (e.g., as described in U.S. Pat. No. 4,449,980), intranasally (e.g., as described in U.S. Pat. No. 4,331,651), or intrarectally in the form of suppositories or pessaries, as is known in the art. The compositions may also be administered orally in formulations designed to survive the stomach for absorption through the gut.

Compositions suitable for use in the present invention may also include other active ingredients, e.g. anti-inflammatory steroids such as natural or synthetic cortisones or derivatives thereof; antibiotics such as tetracyclines, penicillins, cephalosporins, or derivatives thereof; and other antibiotics which may prevent or ameliorate infection at the site of injection or implantation.

Formulations suitable for use in the present invention are made according to methods and procedures well known to those skilled in this art.

Preferably, the compositions of the present inventions are administered in the form of timed-release implants according to methods and formulations known in the art for androgens and other steroids, e.g. U.S. Pat. Nos. 2,824,546; 4,191,741; 3,737,521; 3,991,750; 4,096,239; Christensen et al., *Animal Reproductive Science*, 7, 531–536 (1984); and Kesler et al., *Theriogenology*, 15(3), 327–334 (1981), all incorporated herein by reference. Alternatively, timed-release implantable or injectable compositions comprising biodegradable capsules, spheres, or the like containing androgen according to methods known to those skilled in this art, e.g. Tice et al., *Proc. Intl. Symp. Controlled Release Bioactive Materials*, 12, 108–109 (1985), may be used. In addition to active ingredients, time-release formulations may also contain compounds useful in regulating release of androgen from the formulation.

The above compositions are administered to the mother during pregnancy in amounts sufficient to achieve and maintain circulating levels of androgen in the bloodstream at levels approximately equivalent to those normally circulating in the bloodstream of a normal adult male of the same species as illustrated below. Methods of measuring circulating levels of androgens in normal adult males of each species are known to those in the art.

Accordingly, in a female bovine mammal (cow), a dosage of androgen calculated to maintain the circulating blood levels of androgen at approximately the level of a normal adult bull, e.g. at about 0.5 to about 15 ng/ml, preferably from about 2 to about 10 ng/ml is administered to the mother. For the average cow weighing about 450 kg, this is equivalent to approximately from about 10 to about 150 mg (preferably about 20 mg) per head per day.

For a female ovine mammal (dam), the mother is administered a dosage of androgen calculated to maintain the circulating blood levels at approximately the level of a normal adult ram, e.g. at about 0.5 to about 15 ng/ml, preferably about 2 to about 7 ng/ml. For the average ewe weighing about 50 kg, this is equivalent to approximately from about 7 to about 50 mg (preferably about 10 mg) per head per day.

For a female porcine mammal (sow) the mother is administered a dosage of androgen calculated to maintain the circulating blood levels of androgen at approximately the level of a normal adult boar, e.g. at about 1 to about 20 ng/ml, preferably from about 2 to about 8 ng/ml. For the average sow weighing about 180 kg, this is equivalent to approximately from about 10 to about 100 mg (preferably about 30 mg) per head per day.

There is a critical period during gestation by which implantation must occur to get the desired effects.

If it is desired to improve carcass merit, feed efficiency and to affect fertility, the female fetus must be exposed to an effectively constant amount of androgen prior to the time of the end of the period of the initiation of sexual differentiation. Administration may be initiated during the period of sexual differentiation but most preferably it is initiated before the beginning of the period. The "period of sexual differentiation" as used herein means the period from 40-105 days of gestation in cattle, from 40-60 days of gestation in sheep and from 20-40 days of gestion in pigs.

To reduce birth weight while still achieving subsequent improved growth, the female fetus should be exposed to androgen from about mid-gestation.

Methods of determining the time of onset of sexual differentiation and the various periods of gestation are readily determined by those skilled in the art. In all the above methods, because androgens are known to interfere with parturition, treatment of the pregnant mother with androgens is preferably halted before parturition, most preferably about 5 to about 30 days before delivery. However, as long as administration is begun prior to an above-identified initial period, administration may continue through delivery.

Examples of preferred embodiments are given in Table 1. The indicated dosages (in mg/day) are administered to the mother during the appropriate period of pregnancy (i.e., during the period of gestation given above) to achieve the desired effect:

TABLE 1

|  | carcass merit | sterility | feed efficiency | growth rate | birth weight |
|---|---|---|---|---|---|
| cow | 10-30 | 10-50 | 10-25 | 10-25 | 10-50 |
| ewe | 5-15 | 7-20 | 7-10 | 7-10 | 7-20 |
| sow | 10-60 | 10-75 | 10-35 | 10-35 | 10-75 |

The following non-limiting examples further illustrate the present invention. As used above and below (unless expressly stated to the contrary), all temperatures and temperature ranges refer to the centigrade system and the terms "ambient" and "room temperature" refer to about 20-25° C. The term "percent" or "%" refers to weight percent and the terms mole and moles refer to gram moles.

EXAMPLE 1

Pregnant crossbred ewes were implanted with testosterone propionate beginning at a point between days 40 and 60 of gestation. The implants were made of medical grade Silastic TM [Dow Corning, Midland, Michigan] tubing with an internal diameter of 6.4 mm and an outside diameter of 9.5 mm. A single 10 cm-long implant containing approximately 2.0 grams of testosterone propionate was given to each ewe just under the skin directly posterior to the carpus joint and perpendicular to the 6th and 7th ribs. The implants were designed to allow a controlled release of testosterone propionate resulting in a circulating level of 2 to 3 ng/ml in sheep [Christensen et al., *Animal Reproductive Science*, 7, 531-536 (1984)]. The implants were removed 82 days after implantation.

Twelve ewe and five ram lambs, born from ewes which were implanted, and ten ewe and nine ram lambs, born from non implanted ewes, were studied. Ram and ewe lambs were managed under different conditions. The results are presented in Table 2. In Table 2 yield grade is an estimate of the closely trimmed retail cuts from designated portions of the carcass (equivalent to carcass merit). The results are presented in Table 2.

TABLE 2

|  | birth weight (kg) | avg. daily gain (kg) | 12th rib fat (mm) | rib-eye area (mm$^2$/kg) | yield grade |
|---|---|---|---|---|---|
| Control | 4.95 | 0.179 | 7.62 | 53.08 | 4.01 |
| Treated | 3.73 | 0.206 | 5.54 | 56.25 | 3.23 |

In Table 2 the means in (the birth weight) columns differ ($P<.05$) the avg. (average) daily gain. The means in the yield grade column with unlike superscripts differ ($P<.10$).

Prenatally androgenized ewes had lower birth weights ($P<.05$) than control ewes (3.73 vs 4.95 kg). Birth weights were similar for androgenized rams and control rams (4.59 vs 4.64 kg). Daily gains were greater ($P<.05$) for androgenized ewes compared to control ewes, but similar for androgenized rams and control rams (.340 vs .344 kg/day). Androgenized ewes did not exhibit regular estrus cycles while control ewes exhibited normal estrus cycles. No androgenized ewes became pregnant; however, 8 of 10 control ewes became pregnant. Although differences were not significant, fat thickness measurements were less and ribeye areas were greater for androgenized ewes than control ewes. Yield grades of androgenized ewes were lower ($P<.10$) than control ewes. Birth weights of female lambs were decreased approximately 17% by prenatal androgenization. From birth to 110 pounds (average slaughter weight) ewes which were androgenized in utero grew 13.5% faster than control ewes. It is interesting to note that improved growth continued past weaning, a situation not reported in postnatally-treated animals without continuous treatment at regular intervals over their lifetimes. None of the androgenized ewes showed behavioral estrus or became pregnant, while 80% of the control ewes showed estrus and 70% became pregnant when exposed to a ram. At slaughter, androgenized ewes produced carcasses which were leaner and contained more muscle per unit of body weight than control ewes.

EXAMPLE 2

In a procedure similar to that of Example 1, cows were implanted with testosterone propionate/Silastic implants from approximately day 150 to day 240 of gestation and the implants were removed approximately 3 weeks prior to calving. The implants were 15 cm long and contained approximately 2.5 grams testosterone propionate per implant. Each cow was implanted subcutaneously with two implants, one behind each shoulder about 10 cm below the spine. The implants were designed to allow a controlled release of testosterone propionate resulting in a circulating level of 1 to 2 ng/ml in cattle [Kesler et al., *Theriogenology*, 15(3), 327–334 (1981)].

Results are shown in Table 3 in which the means in the gain feed ratio column are statistically different at $P<.10$.

TABLE 3

|  | birth weight (lbs) | weight per day of age to weaning (lbs) | 12th rib fat (mm) | ribeye area (mm$^2$/kg) | yield grade | gain: feed ratio |
| --- | --- | --- | --- | --- | --- | --- |
| Control cows | 84.0 | 2.51 | 11.43 | 26.92 | 2.60 | 0.106 |
| Androgenized cows | 76.6 | 2.57 | 10.58 | 28.75 | 2.18 | 0.134 |

The means in the gain:feed ratio column are statistically different at $P<.10$.

Birth weights of calves were decreased approximately 8% by prenatal androgenization. Heifers which were androgenized prenatally had an weaning weight an average of 23 pounds heavier than control heifers. Rate and efficiency of gain were each improved approximately 8% for the first 72 days in the feedlot.

EXAMPLE 3

The procedure of Example 1 was repeated with a different group of control and treated ewes. Thirty-seven ram lambs and 29 ewe lambs were obtained from untreated (control) mothers and 25 ram lambs and 28 ewe lambs were obtained from treated mothers. The results after 28 days in the feedlot are given in Table 4:

TABLE 4

|  | daily gain (lbs/day) | gain:feed ratio |
| --- | --- | --- |
| Control ewes | 0.576 | 0.189 |
| Treated ewes | 0.608 | 0.210 |

These data corroborate results of Example 1 in improved rate of gain and feed efficiency without undesired complete masculinization.

EXAMPLE 4

Six non-pregnant ewes were used for a study of the effect of controlled release versus uncontrolled release of androgen. Four testosterone compressed pellets were manufactured with a hand pellet press and testosterone (mean = 1.001g/pellet; C.V. = 1.03%). Three ewes were implanted with one implant each in the neck. Three silicone/testosterone propionate (testosterone propionate) implants were manufactured as previously described (approximately 1.5 g of testosterone propionate/implant; C.V. = 0.75%). Three ewes were implanted with one implant each in the axilla. All implants were implanted with one implant each in the axilla. All implants were left in situ for 50 days. After removal the implants were dried under heat for 24 hours and weighed to determined hormone loss in vivo.

Immediately before implantation (time 0), 1, 2, and 4 hours, 1, 3, 7, 10, 14, 17, 21 and 50 (4 samples over 4 hours) days after implantation blood samples were collected for testosterone determination via a validated enzyme immunoassay.

The testosterone pellets released 357.8 mg of testosterone (C.V. = 73.45%). The testosterone propionate/silicone implants secreted 444.2 mg of testosterone propionate (C.V. = 13.44%). This is equivalent to 371.9 mg or testosterone which is within 4.0% of the quantity of testosterone released from the testosterone pellets.

Testosterone concentrations across time are illustrated in the Figure. There was a massive burst release detected for the ewes implanted with the pellets which was not detected for the ewes implanted with the testosterone propionate/silicone implants. Even though nearly equivalent quantities of testosterone were released from the implants, blood testosterone concentrations were consistently higher across days post-implantation for the testosterone propionate/silicone implanted ewes (dots) than for the testosterone pellet implanted ewes (X's). Testosterone concentrations for the ewes with testosterone pellets were over 2.5 times more variable than for ewes with testosterone propionate/silicone implants (C.V. = 45.19% vs. C.V. = 17.38%).

The quantity of testosterone released from the testosterone pellets was similar to that observed Clarke et al., *J. Embryol, Exp. Morph.*, 36, 87–99 (1976). Clarke and his co-workers reported an average release of 357.5 mg over the 50 day implantation period. Clarke and co-worker reported mean blood testosterone concentrations of 3.8 to 11.4 ng/ml on the day of implant removal. In our study testosterone concentrations were generally within this range but tended to be somewhat lower. However, there are differences of this nature between different immunoassays.

In summary, testosterone propionate/silicone implants release hormone more consistently without the burst observed when pellet implants were used.

EXAMPLE 5

Exposure of unborn female calves to testosterone propionate (prenatal androgenization) increases postnatal growth. In the foregoing examples, testosterone propionate has been initiated at varying stages of gestation. If testosterone propionate treatment must be initiated early in gestation, then the treatment may be difficult to implement in some commercial applications. Past studies have been focused on the growth potential of the prenatally-androgenized female offspring. The purpose of this preliminary study was to determine the effect of testosterone propionate treatment initiated prior to the breeding season on the ability of females to conceive and to determine the fertility of the resulting female offspring.

Twenty-five crossbred beef heifers, approximately 15 months of age were randomly assigned to treated (n=13) or control (n=12) groups. The treated heifers were subcutaneously implanted with four capsule-type testosterone propionate implants made from medical grade silastic tubing with an internal diameter of 0.635 cm and an external diameter of 0.9525 cm. Each implant was 15 cm in length and contained approximately 2.25 gm of testosterone propionate. The implants were placed behind the shoulder and over the ribs. Three days after the treated heifers were implanted all females were exposed to a single Angus bull for 75 days. On days 36 and 102 after the beginning of the breeding season, serum samples were collected for testosterone and/or progesterone determinations. Approximately 6 weeks prior to calving the testosterone propionate implants were removed.

The following spring the number and sex of the resulting offspring were recorded and all calves determined to be female were phenotypically female and were retained for further study. At approximately 13 months of age the female offspring (from both the control and testosterone propionate treated dams) were treated for estrous synchronization. Thirteen days after the end of the estrous synchronization, serum samples were collected for progesterone determination to determine if the heifers had ovulated. At approximately 15 months of age the control and prenatally testosterone treated heifers were again synchronized. All females were artificially inseminated to an Angus bull. On days 5 and 12 after artificial insemination, serum samples were collected for progesterone determination to compare luteal progesterone concentrations between control and treated heifers. Females detected in estrus in the next 30 days were artificially inseminated. On day 30, females were exposed to a mature Angus bull for the remainder of the 65 day breeding season. Pregnancy status was determined by rectal palpation of the reproductive tract 45 days after the end of the breeding season. The results are provided in Tables 4–6.

TABLE 4

EFFECT OF TESTOSTERONE PROPIONATE ON TESTOSTERONE AND PROGESTERONE CONCENTRATIONS DURING THE BREEDING SEASON

| Treatment Group | n | Testosterone Concentrations (ng/ml) | | Progesterone Concentrations (ng/ml) of Pregnant Females |
|---|---|---|---|---|
| | | Day 39 | Day 105 | Day 105 |
| Control | 12 | .15 | .18 | 6.95 |
| Treated | 13 | 3.82 | 3.47 | 4.97 |

In Table 4, it is shown that testosterone propionate implants were effective in elevating testosterone concentrations for an extended period of time. In pregnant females progesterone concentrations may be sightly depressed by testosterone propionate treatment.

TABLE 5

EFFECT OF TESTOSTERONE PROPIONATE TREATMENT, INITIATED PRIOR TO THE BREEDING SEASON, ON FERTILITY AND CALVING

| Treatment Group | n | Pregnant % | Male Calves | Female Calves | Average Birth Date of Calves |
|---|---|---|---|---|---|
| Control | 12 | 11(92) | 7 | 4 | Feb. 10 |

TABLE 5-continued

EFFECT OF TESTOSTERONE PROPIONATE TREATMENT, INITIATED PRIOR TO THE BREEDING SEASON, ON FERTILITY AND CALVING

| Treatment Group | n | Pregnant % | Male Calves | Female Calves | Average Birth Date of Calves |
|---|---|---|---|---|---|
| Treated | 13 | 4(31) | 1 | 3 | Feb. 17 |

The percent of pregnancy in control and treated groups is significantly different ($P<.005$).

When testosterone propionate administration is initiated prior to the breeding season it decreases the number of females that become pregnant during the breeding season (Table 5). Testosterone treatment had no effect on the conception data of the females that became pregnant (reflected by calving dates). The treatment had no effect on the sex of the resulting offspring.

TABLE 6

EFFECT OF PRENATAL ANDROGENIZATION ON FERTILITY OF BEEF FEMALES

| Treatment Group | n | High Progesterone at 13 months of Age (%) | Progesterone Concentrations ng/ml | | Pregnant at End of Breeding Season (%) |
|---|---|---|---|---|---|
| | | | Day 5 | Day 12 | |
| Control | 4 | 4(100) | 3.25 | 6.56 | 4(100) |
| Treated | 3 | 3(100) | 4.34 | 9.58 | 2(67) |

In Table 6 the "high progesterone" column shows the percent of heifers having high ($>1.5$ ng/ml) progesterone on day 13 following estrous synchronization.

In Table 6 it can be seen that testosterone propionate treatment did not adversely effect fertility of the prenatally androgenized heifers. Following estrous synchronization at 13 months of age all of the heifers ovulated. At 15 months of age progesterone levels of day 5 and day 12 of the cycle were similar for treated and control heifers. During the 65 day breeding season four (100%) of the control heifers became pregnant and two (67%) of the treated heifers became pregnant.

The results indicate that females are capable of conceiving in the presence of testosterone propionate but at a reduced rate. Females prenatally treated with testosterone are capable of conceiving with two of the three prenatally testosterone treated heifers becoming pregnant during the breeding season.

Thus cows treated with testosterone propionate implants prior to the breeding season and may become pregnant. Fertility during the breeding season is lower than that for untreated control animals. The average date of conception is not different than that of the controls. Of the females that did become pregnant, the treatment non-significantly lowered progesterone levels at day 105 after testosterone propionate treatment. Testosterone propionate treatment did not effect the sex of the resulting offspring. At 13 months of age the female offspring (prenatally testosterone-treated) ovulated following estrous synchronization. The prenatally androgenized heifers had progesterone levels similar to controls on days 5 and 12 of the estrous cycle at 15 months of age. During a 65 day breeding season 4/4 of the control heifers became pregnant, while ⅔ of the prenatally testosterone treated heifers became pregnant.

These results show that no matter how early relative to sexual differentiation androgen is administered, fertile phenotypic females may be obtained.

EXAMPLE 6

In a study to investigate the effect of prenatal androgenization on the fertility of yearling beef females, sixty-five untreated and 50 prenatally-androgenized beef heifers at two locations were synchronized with Syncro-Mate B and artificially inseminated 47 hours after implant removal. All heifers that returned to estrus in the first 25 days of the breeding season were inseminated a second time. In Trial 1 natural service was used for the remainder of the 60 day breeding season, while artificial insemination was used as the method of rebreeding in a 70 day breeding season in Trial 2. Pregnancy rates (first service and end of the breeding season) were higher for prenatally androgenized heifers than for control heifers at both locations. Therefore, prenatal androgenization does not adversely affect fertility.

Crossbred beef females (n=235) were randomly assigned t o treated or control groups 30 days after the end of a 60 day breeding season. Treated females were administered 4 testosterone propionate (testosterone propionate) implants each. The implants were made of a medical grade silicone tubing with an internal diameter of 0.635 cm and an external diameter of 0.953 cm. Implants were 15 cm in length and contained approximately 2.25 g of testosterone propionate. Implants were subcutaneously inserted behind the shoulder and over the dorsal aspect of the rib cage. Implants were removed approximately 3 weeks prior to the onset of the calving season.

The resulting prenatally-androgenized (offspring of testosterone propionate-treated cows; n=50) and control heifers (n=66) were weaned from their dams at approximately 7 months of age and were retained as replacement heifers for the beef herd. This study was conducted in two trials. Trial 1 was conducted at the beef unit at the Dixon Springs Agricultural Center at Simpson, Illinois and Trial 2 was conducted at the Orr Beef Research Center at Perry, Illinois.

Prior to and during the breeding season, control and treated heifers were maintained together. In both trials, estrus was synchronized with Syncro-Mate B. The Syncro-Mate B procedure consists of a norgestomet implant which is subcutaneously inserted into the convex surface of the ear. At the time of implant insertion an intramuscular injection of 5.0 mg of estradiol valerate and 3.0 mg of norgestomet was administered. The norgestomet implant was removed at the end of 9 days. Approximately 47 hours after implant removal all heifers were artificially inseminated.

In Trial 1, heifers that returned to estrus in the first 25 days of the breeding season were artificially inseminated a second time. Natural service was used on days 25-60 of the breeding season. In Trial 2, estrus detection and artificial insemination were used throughout a 70 day breeding season. Rectal palpation of the reproductive tract was conducted on days 63 and 153 after the initial artificial insemination to determine pregnancy rate to the synchronized artificial insemination and overall pregnancy rate.

The results are summarized in Table 7. "Treated" heifers were prenatally androgenized. The "First Service Pregnancy Rate" conception rate to the initial Syncro-Mate B timed artificial insemination. One control heifer lost the Syncro-Mate B implant and was not included in the first service rate.

TABLE 7
EFFECT OF PRENATAL ANDROGENIZATION ON REPRODUCTIVE PERFORMANCE OF BEEF HEIFERS

| Trial | Control | Treated |
|---|---|---|
| First Service Pregnancy Rate (%) | | |
| 1 | 17/49(35) | 15/33(45) |
| 2 | 4/16(25) | 8/17(47) |
| Combined | 21/65(32) | 23/50(46) |
| Pregnancy Rate-End of Breeding Season (%) | | |
| 1 | 37/50(74) | 27/33(82) |
| 2 | 10/16(63) | 13/17(76) |
| Combined | 47/66(71) | 40/50(80) |

The results were similar at both locations. Prenatal androgenization clearly had no adverse affects on reproductive function. In fact, fertility may be been enhanced by prenatal androgenization. Prenatal androgenization does not adversely affect reproductive function.

Further experiments of the sort described in Example 6 have resulted in a cumulative conception rate of 35/106 (33%) for control animals and 39/80 (49%) for treated animals. The difference between these rates is significant at $P<.05$.

Further examples within the spirit and the scope of the invention will occur to those skilled in the art, and only those limitations appearing in the claims should be read thereon.

We claim:

1. A method for obtaining fertile, phenotypically female offspring despite androgen exposure during gestation comprising the step of:
   administering to a pregnant female, by about the initiation of sexual development for at lest 14 days and up to delivery an effectively constant amount of androgen by a timed release system, wherein the circulating level of androgen in the blood of the pregnant female is maintained in the lower half of the range of androgen levels of female offspring are achieved.

2. The method as recited in claim 1 wherein said maintaining step comprises the step of controlling the circulating level of androgen to be in the lowermost quarter of the range of androgen levels of the normal adult male.

3. The method as recited in claim 1 wherein said administering step is begun prior to the time of initiation of sexual development.

4. The method as recited in claim 1 wherein said administering step is maintained through the end of gestation.

5. The method as recited in claim 1 wherein said administering step is maintained through the second third of gestation.

6. The method as recited in claim 1 wherein said administering step is maintained through mid gestation.

7. The method as recited in claim 1 wherein said administering step is maintained through about one week before parturition.

8. The method as recited in claim 1 wherein said administering step is maintained for 14-30 days.

* * * * *

UNITED STATES PATENT AND TRADEMARK OFFICE
CERTIFICATE OF CORRECTION

PATENT NO. : 5,238,928
DATED : August 24, 1993
INVENTOR(S) : Larry L. Berger and Darrel Kesler It is certified that error appears in the above-indentified patent and that said Letters Patent is hereby corrected as shown below:

Column 12, line 43, should read --the range of androgen levels of a normal adult male wherein the male and female are from the same species selected from the group consisting of bovine, ovine and porcine species, whereby an increase in carcass merit, feed efficiency and growth rate of female offspring are--

Column 12, line 38, "lest" should be "least".

Signed and Sealed this

Twelfth Day of April, 1994

Attest:

BRUCE LEHMAN

*Attesting Officer*      *Commissioner of Patents and Trademarks*